United States Patent
Wu et al.

(10) Patent No.: US 6,875,771 B2
(45) Date of Patent: Apr. 5, 2005

(54) PYRIDOPYRIMIDINE DERIVATIVES AS 5-HT$_6$ ANTAGONISTS

(75) Inventors: Yong-Jin Wu, Madison, CT (US); Shuanghua Hu, Milford, CT (US); Paul M. Scola, Glastonbury, CT (US); Yazhong Huang, West Haven, CT (US); Katharine A. Grant-Young, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/620,240

(22) Filed: Jul. 15, 2003

(65) Prior Publication Data

US 2004/0019064 A1 Jan. 29, 2004

Related U.S. Application Data

(60) Provisional application No. 60/398,929, filed on Jul. 26, 2002.

(51) Int. Cl.$^7$ ..................... C07D 487/02; A61K 31/519
(52) U.S. Cl. ............................. 514/259.4; 514/259.41; 514/267; 544/250; 544/252; 544/282
(58) Field of Search ................................ 544/250, 252, 544/282; 514/259.4, 259.41, 267

(56) References Cited

U.S. PATENT DOCUMENTS

| | | | |
|---|---|---|---|
| 5,990,105 A | 11/1999 | Bös et al. | 514/235.5 |
| 6,441,013 B1 | 8/2002 | Greiner et al. | 514/241 |

FOREIGN PATENT DOCUMENTS

| | | |
|---|---|---|
| EP | 0 930 302 | 7/1999 |
| EP | 0 941 994 | 9/1999 |
| WO | WO 0037452 | 6/2000 |

OTHER PUBLICATIONS

Huggins, Serotonin Receptors and the Effects of Ecstasy, Stanislaus Journal of Biochemical Reviews, May 2001.*
Damasio, Alzheimer's Disease and Related Dementias, Cecil Textbook of Medicine, 20$^{th}$ Edition, vol. 2, pp. 1992–1996, 1996.*
Layzer, Degenerative Diseases of the Nervous System, Cecil Textbook of Medicine, 20$^{th}$ Edition, vol. 2, pp. 2050–2057, 1996.*
Bentley, J. C., et al., *British J. Pharm.* (1999) 126:1537–1542.
Bourson, A. et al., *J. Pharmacol. Exp. Ther.* (1995) 274(1):173–180.
Monsma, F. J. et al., *Mol. Pharmacol.* (1993) 43:320–327.
Murata, S. et al., *British J. of Pharmocol.* (1999) 127:19–26.
Rogers, D.C. and Hagan J.J., *Psychopharmacology* (2001) 158:114–119.
Roth, B. L. et al., *J. Pharmacol. Exp. Ther.* (1994) 268(3):1403–1410.
Sleight, A. J. et al. *Behav. Brain Res.* (1996) 73: 245–248.
Ward, R. P. et al., *Neuroscience* (1995) 64(4):1105–1111.
Woolley, M.L. et al., *Neuropharmacology* (2001) 41:210–219.

* cited by examiner

Primary Examiner—Deepak Rao
(74) Attorney, Agent, or Firm—Aldo A. Algieri

(57) ABSTRACT

Novel pyridopyrimidine derivatives which have a binding affinity for the human 5-HT$_6$ receptor and, therefore, are useful in treating disorders responsive to antagonism of the 5-HT$_6$ receptor such as psychosis, schizophrenia, manic depression, depression, neurological disorder, memory disorder, Parkinson's disease, amyotrophic lateral sclerosis, Alzheimer's disease and Huntington's chorea.

9 Claims, No Drawings

PYRIDOPYRIMIDINE DERIVATIVES AS 5-HT₆ ANTAGONISTS

CROSS-REFERENCE TO RELATED APPLICATIONS

This is a non-provisional application which claims the benefit of U.S. Provisional Application No. 60/398,929 filed Jul. 26, 2002.

FIELD OF THE INVENTION

The present invention is directed to novel pyridopyrimidine derivatives which have a selective affinity to 5-HT₆ receptors and are accordingly suitable for the treatment and prevention of central nervous disorders such as psychoses, schizophrenia, manic depression, depression, neurological disorders, memory disorders, Parkinson's disease, amyotrophic lateral sclerosis, Alzheimer's disease and Huntington's chorea. The present invention is also directed to a method of treatment with the novel compounds and to pharmaceutical compositions containing them.

BACKGROUND OF THE INVENTION

The neurotransmitter 5-hydroxytryptamine (serotonin), acting through its binding to a family of receptors, has been implicated in the regulation of a wide variety of biological responses including mood, temperature regulation, pain perception, feeding, sleeping, and learning and memory. Aberrant regulation serotonergic-mediated signaling is also believed to play a critical role in a number of disease processes including affective disorders, migraine, schizophrenia, and cognition processes. In addition, many compounds that are used therapeutically interact with the serotonergic system either through direct interaction with serotonergic receptors or through proteins that modulate serotonin synthesis, reuptake, and breakdown.

The 5-HT₆ receptor is expressed selectively in the central nervous system and is likely to be involved in mediating the actions of serotonin in many of these processes (Mol. Pharm. 1993, 43, 320–327). Disruption of 5-HT₆ receptor expression, or blockade of 5-HT₆ receptor signaling, produces a behavioral syndrome that is reversed by centrally-acting muscarinic antagonists, suggesting that the 5-HT₆ receptor is involved in the negative regulation of acetylcholine-mediated neurotransmission (JPET 1995, 274, 173–180; Behav. Brain Res. 1996, 73, 245–248; British J. Pharm. 1999, 126, 1537). Patients with Alzheimer's disease exhibit a gradual loss of cognitive ability that correlates with a decrease in cholinergic neurotransmission. It is anticipated that a selective 5-HT₆ receptor antagonist will improve cognitive function in Alzheimer's disease patients by enhancing cholinergic signaling.

Consistent with this hypothesis, preliminary evidence suggests pharmacological blockade of 5-HT₆ receptors results in an increased ability of animals to perform in cognition models (British J. Pharm. 1999, 127, 21P; British J. Pharm. 1999, 127, 22P). Compounds which have a selective affinity to 5-HT₆ receptors may therefore be suitable for the treatment and prevention of central nervous disorders such as psychoses, schizophrenia, manic depression (Roth, R. L. et al., J. Pharmacol. Exp. Ther. 1994, 268, 1403–1410), depression (Sibley, D. R. et al., Mol. Pharmacol. 1993, 43, 320–327), neurological disorders (Bourson, A. et al., J. Pharmacol. Exp. Ther. 1995, 274, 173–180; Ward, R. P. et al., Neuroscience 1995, 64, 1105–1110), memory disorders, Parkinson's disease, amyotrophic lateral sclerosis, Alzheimer's disease and Huntington's chorea (Sleight, A. J. et al., Neurotransmissions 1995, 11, 1–5). Therefore, based upon the localization of 5-HT₆ receptors in the brain, and the wide variety of responses regulated by serotonin, there appears a need to discover novel small molecule 5-HT₆ antagonists in order to treat a number of human disorders.

European Patent Application EP 0 941 994 A1, published Sep. 15, 1999, discloses pyrazolopyrimidines and pyrazolotriazines having a selective affinity to 5-HT₆ receptors, of the general formulae I-A and I-B shown below:

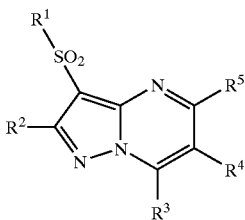

I-A

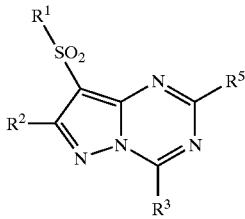

I-B which are suitable for the treatment and prevention of central nervous system disorders. For formulae I-A and I-B, $R^1$ is phenyl, optionally substituted by one or more lower alkyl, halogen, lower alkoxy, tolyl, pyridyl, napthyl or thiophenyl; $R^2$ is hydrogen, lower alkyl, lower thioalkyl, or hydroxy-lower alkoxy; $R^3$ is amino, lower alkylamino, di-lower-alkyl-amino, piperazinyl, optionally substituted by one or more lower alkyl, benzyl, phenyl or hydroxy-lower-alkyl, morpholinyl, imidazolyl, $(CH_3)_2N(CH_2)_nNH$—, $(CH_3)_2N(CH_2)_nO$— or morpholinyl-$(CH_2)_nO$— in which n is 2 or 3; $R^4$ is hydrogen, lower alkyl or hydroxy-lower alkyl; $R^5$ is hydrogen, halogen, lower alkyl, $C_3$–$C_6$-cycloalkyl, lower-alkyl-lower-alkoxy, hydroxy-lower-alkyl-lower-alkoxy, $(CH_3)_2N(CH_2)_nNH$—, piperazinyl, optionally substituted by lower alkyl, methyl-piperazinyl, optionally substituted by lower alkyl, morpholinyl, methyl-morpholinyl, di-lower-alkylamino or di-lower-alkylamino-lower-alkyl, or $R^4$ and $R^5$ together are —$(CH_2)_m$— or $CH_2$—S—$CH_2$— wherein m is 3 or 4 as well as their pharmaceutically acceptable salts.

U.S. Pat. No. 5,990,105, issued Nov. 23, 1999, to Bos et al. and European Patent Application No. EP 0 930 302, published Jul. 21, 1999, disclose benzosulfone derivatives useful in treating central nervous system disorders of the general formula:

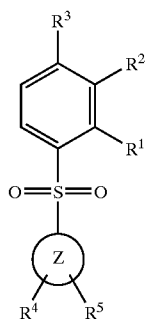

wherein R¹ is hydrogen; R² is hydrogen, trifluoromethyl or lower alkyl; R³ is hydrogen or amino; or R¹ and R² or R³ and R² taken together are —CH=CH—CH=CH—; Z is pyrimidin-4-yl, pyridin-4-yl, pyridin-2-yl or phenyl; R⁴, R⁵ are each independently hydrogen, lower alkyl, trifluoromethyl, halogen, lower alkoxy, nitrilo, amino, lower alkyl-amino, di-lower alkyl-amino, piperazinyl, morpholinyl, pyrrolidinyl, vinyl, $C_3$–$C_6$ cycloalkyl, $C_3$–$C_6$ cycloalkenyl, t-butylethinyl, hydroxyalkylethinyl, phenylethinyl, napthyl, thiophenyl, or phenyl, which may be substituted by halogen, lower alkoxy, lower alkyl, trifluoromethyl or nitro, or a group —NH(CH$_2$)$_n$NR⁶R⁷, —N(CH$_3$)(CH$_2$)$_n$NR⁶R⁷, —NH(CH$_2$)$_n$-morpholin-4-yl or —NH(CH$_2$)$_n$OH; n is 2–4; R⁶ and R⁷ are each independently hydrogen or lower alkyl, and pharmaceutically acceptable salts thereof.

PCT Application No. WO 0037452, published Jun. 29, 2000, discloses sulfonyloxazolamines useful in treating conditions implicating the 5-HT$_6$ receptor of the following general formula:

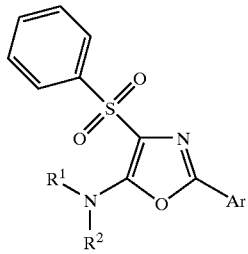

wherein R¹ and R² are each independently hydrogen, A, —(CH$_2$)$_n$—Ar, or $C_2$–$C_6$ alkenyl; or R¹ and R² taken together represent a mononuclear saturated heterocycle with one to two heteroatoms; Z is hydrogen, A, CF$_3$, NO$_2$, halogen, hydroxy, OA, NH$_2$, NHA or NA$_2$; A represents $C_1$–$C_6$ alkyl; and Ar is Z-monosubstituted or Z-disubstituted phenyl.

The foregoing disclosures do not teach or suggest the novel pyridopyrimidine derivatives of the present invention. The novel compounds of the present invention display 5-HT$_6$ receptor activity.

SUMMARY OF THE INVENTION

This invention provides a novel series of compounds of Formula I:

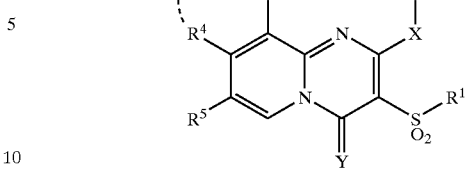

wherein R¹, R², R³, R⁴, R⁵, X and Y are as defined below including pharmaceutically acceptable salts, hydrates, and solvates thereof, which bind to human 5-HT$_6$ receptors and, as thus, are useful in treating disorders of the central nervous system where the 5-HT$_6$ receptor is implicated.

DETAILED DESCRIPTION OF THE INVENTION

The present invention provides novel pyridopyrimidine derivatives which have been found to be 5-HT$_6$ receptor antagonists. The present invention also provides pharmaceutical compositions containing the novel pyridopyrimidine derivatives and a method of treating diseases or disorders responsive to 5-HT$_6$ receptor antagonism such as psychoses, schizophrenia, manic depressions, depressions, neurological disorders, memory disorders, Parkinson's disease, amyotrophic lateral sclerosis, Alzheimer's disease and Huntington's chorea.

The novel pyridopyrimidine derivatives of the present invention are represented by Formula I:

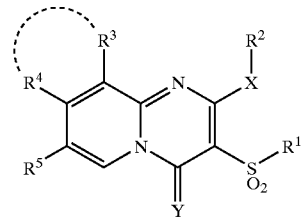

wherein:
R¹ is napthyl or phenyl, said phenyl optionally substituted with one to three substituents each independently selected from the group consisting of halogen, $C_{1-4}$ alkyl, and trifluoromethoxy;
R² is 5-methylpyridin-2-yl or $C_{1-4}$ alkyl, said $C_{1-4}$ alkyl optionally substituted with hydroxy;
R³ is hydrogen, halogen, $C_{1-4}$ alkyl, or benzyloxy;
R⁴ is hydrogen or $C_{1-4}$ alkyl;
the dashed line, taken with R³ and R⁴ together, optionally forms a 5 to 6 member aromatic ring structure having zero to 2 heteroatoms;
R⁵ is hydrogen, halogen, $C_{1-4}$ alkyl, benzyl, or C(O)R⁸;
X is NR⁶, O, or S(O)$_m$;
Y is NR⁷ or O;
m is 0, 1 or 2;
R⁶ is hydrogen or $C_{1-4}$ alkyl;
R⁷ is hydrogen, $C_{1-4}$ alkyl, or C(O)$C_{1-4}$ alkyl; and
R⁸ is $C_{1-4}$ alkoxy, amino, ($C_{1-4}$ alkyl)amino, di($C_{1-4}$ alkyl)amino, or hydroxy; or a nontoxic pharmaceutically acceptable salt or solvate thereof.

The term "$C_{1-4}$ alkyl" as used herein and in the claims (unless the context indicates otherwise) means straight or branched chain alkyl groups such as methyl, ethyl, propyl, isopropyl, butyl, isobutyl, t-butyl and the like.

The term "$C_{1-4}$ alkoxy" as used herein and in the claims (unless the context indicates otherwise) means straight or branched chain alkoxy groups such as methoxy, ethoxy, propoxy, isopropoxy, butoxy, isobutoxy, t-butoxy and the like.

The term "halogen" as used herein and in the claims is intended to include bromine, chlorine, fluorine and iodine.

The term "nontoxic pharmaceutically acceptable salt" as used herein and in the claims is intended to include nontoxic acid addition salts. Suitable acids include sulfuric, phosphoric, hydrochloric, hydrobromic, hydroiodic, citric, acetic, benzoic, cinnamic, fumaric, mandelic, tartaric, maleic, phosphoric, nitric, mucic, isethionic, palmitic, heptanoic, and the like.

Generally, pharmaceutically acceptable salts of the invention are those in which the counter-ion does not contribute significantly to the toxicity or pharmacological activity of the salt. In some instances, they have physical properties which make them more desirable for pharmaceutical formulations, such as solubility, lack of hygroscopicity, compressibility with respect to tablet formation and compatibility with other ingredients with which the substance may be used for pharmaceutical purposes. The salts are routinely made by admixture of a Formula I compound with the selected acid, preferably by contact in solution employing an excess of commonly used inert solvents such as water, ether, toluene, dioxane, methanol, ethanol, ethyl acetate and acetonitrile. They may also be made by metathesis or treatment with an ion exchange resin under conditions in which the appropriate ion of a salt of the substance of the Formula I is replaced by another ion under conditions which allow for separation of the desired species such as by precipitation from solution or extraction into a solvent, or elution from or retention on an ion exchange resin.

Certain compounds of the present invention can exist as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be within the scope of the present invention.

In the method of the present invention, the term "therapeutically effective amount" means the total amount of each active component of the composition that is sufficient to show a meaningful patient benefit, i.e., healing or prevention of conditions characterized by antagonism of the $5\text{-HT}_6$ receptor or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat, treating, treatment" as used herein and in the claims means preventing or ameliorating diseases, and/or symptoms by antagonism of the $5\text{-HT}_6$ receptor in a mammal in need thereof, by administration of a compound of Formula I.

When Y is oxygen, the keto compounds of Formula I are represented by the following structure:

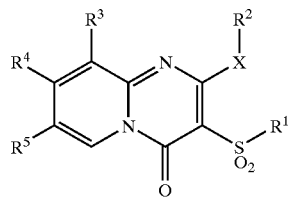

wherein $R^1$, $R^2$, $R^3$, $R^4$, $R^5$ and X are as defined above.

When Y is $NR^7$, the imido compounds of Formula I are represented by the following structures:

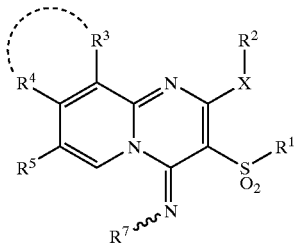

wherein $R^1$, $R^2$, $R^3$, $R^4$, $R^5$, $R^7$, the dashed line, and X are as defined above.

Certain compounds of the present invention possess an imine moiety when Y is $NR^7$. The imine moiety can have either an entgegen (i.e. opposite or (E)) or a zusammen (i.e., together or (Z)) configuration as depicted below. It is to be understood that the compounds with either the individual (E) or (Z) configuration or any mixture thereof, as shown below, are intended to be within the scope of the present invention.

(E)

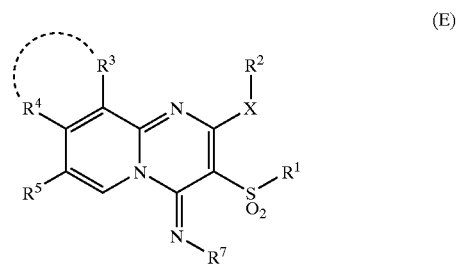

(Z)

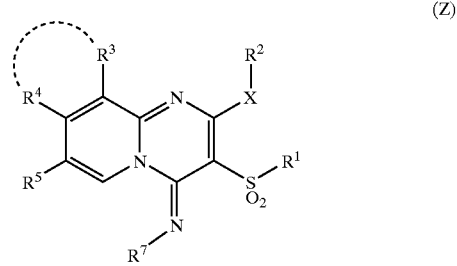

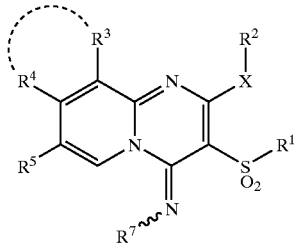

mixture of (E) and (Z)

The compounds of Formula I and intermediates useful for their synthesis may be prepared by various procedures such as those illustrated herein in Reaction Schemes 1 and 2, Examples 1 through 35, and by variations thereof which would be evident to those skilled in the art.

The present invention also relates to a method of preparing a compound of Formula I as illustrated in Reaction Schemes 1 and 2 below.

Reaction Scheme 1:

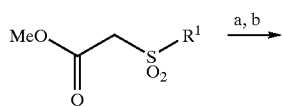

Reaction Scheme 2:

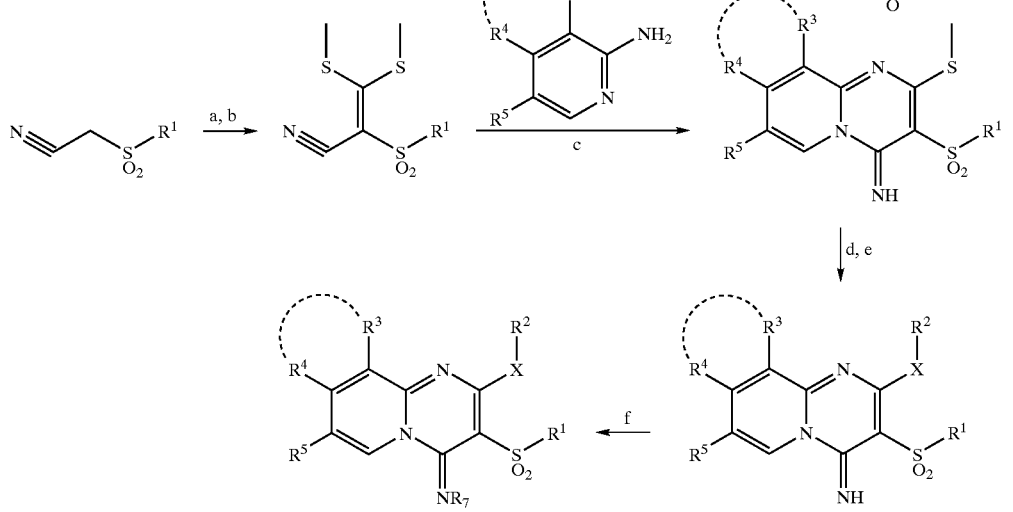

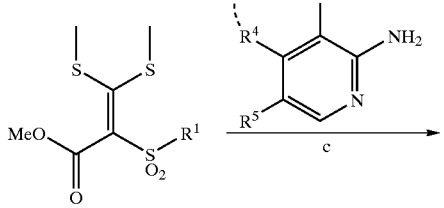

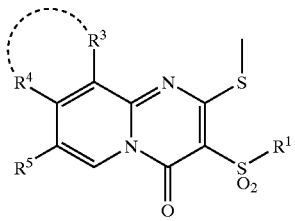

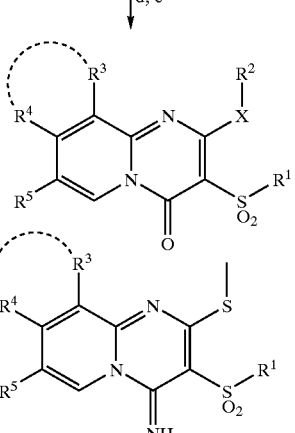

Conditions:
a) $CS_2$, base, DMSO
b) $CH_3I$
c) base, if needed; 80°
d) $HXR^2$
e) $Hg(OAc)_2$
f) $R^7$—X To a solution of 1.0 equivalent of the appropriate phenyl sulfonyl acetyl acetate derivative (as in Reaction Scheme 1) or phenylsulfonyl acetonitrile derivative (as in Reaction Scheme 2) in anhydrous dimethylsulfoxide (DMSO), is added 1.0 equivalent of carbon disulfide ($CS_2$), and the mixture is stirred for ten minutes at room temperature. The reaction mixture is then cooled to approximately 0° C. and 2.0 equivalents of an appropriate base, such as an alkali hydride, preferably sodium hydride, is added in one portion. The resulting reaction mixture is stirred until homogeneous and allowed to warm to room temperature for one hour. The reaction mixture is cooled again to 0° C. and 2.0 equivalents of iodomethane is added under argon. The reaction mixture is allowed to warm to room temperature with stirring over 12 to 24 hours. Water is added and the resulting slurry is stirred for 15 minutes. The resulting solid is collected by filtration, washed with deionized water, and allowed to dry. The crude product is taken up in an appropriate solvent or solvent mixture, such as 25% hexanes in chloroform, and purified by flash chromatography to provide the appropriate purified 3,3-dimethylthiophenylsulfonyl intermediate.

To a solution of 1.0 equivalent of the appropriate 3,3-dimethylthioarylsulfonyl intermediate and 1–5 equivalents of an appropriate 2-aminopyridine derivative in dimethylformamide (DMF) or dioxane is added 1.0 equivalent of an appropriate base, if necessary. The reaction mixture is heated at approximately 80° C. for 1 to 2 days then cooled to room temperature. The reaction mixture is then diluted with an appropriate solvent, such as methanol or acetonitrile, and purified on a reverse phase preparative HPLC column (XTerra™ MS C18 5.0 mM 19×150 mm, for example) to provide the purified methylthiophenylsulfonylpyridopyrimid-4-imine or methylthiophenylsulfonylpyridopyrimid-4-one intermediate.

Nucleophilic displacement of the thiomethyl group of the preceding intermediate was effectuated with an appropriate amine, alcohol or thiol of general formula $HXR^2$ in which X is $NR^6$, O, or S, respectively. The reaction was carried out by treating the methylthiophenylsulfonylpyridopyrimid-4-imine or methylthiophenylsulfonylpyridopyrimid-4-one intermediate with 1.0 equivalent of an appropriate amine of the general formula $HXR^2$ in which X represents $NR^6$, in an appropriate solvent, such as DMF, with mercury (II) acetate $(Hg(OAc)_2)$ at room temperature for a period of 10 minutes to 1 hour. The resulting product is purified by standard methods such as preparative HPLC or column chromatography.

Alternatively, the methylthiophenylsulfonylpyridopyrimid-4-imine or methylthiophenylsulfonylpyridopyrimid-4-one intermediate may be reacted with a slight excess molar equivalent of an appropriate amine, alcohol or thiol of general formula $HXR^2$. The reaction may be carried out in an appropriate solvent, such as DMF, or carried out using an appropriate nucleophile (such as methanol or ethanol) of the general formula $HXR^2$ as the solvent. The reaction is typically run at 55 to 90° C. for a period of 12 to 96 hours.

Preferred compounds of Formula I include
N-(3-benzenesulfonyl-4-imino-4H-pyrido[1,2-a]pyrimidin-2-yl)methylamine;
3-benzenesulfonyl-7-methyl-2-methylsulfanyl-pyrido[1,2-a]pyrimidin-4-ylideneamine;
N-(3-benzenesulfonyl-4-imino-4H-pyrido[1,2-a]pyrimidin-2-yl)ethylamine;
3-benzenesulfonyl-2-ethoxy-pyrido[1,2-a]pyrimidin-4-ylideneamine;
3-benzenesulfonyl-7-bromo-9-methyl-2-methylsulfanyl-pyrido[1,2-a]pyrimidin-4-ylideneamine;
3-benzenesulfonyl-9-bromo-7-methyl-2-methylsulfanyl-pyrido[1,2-a]pyrimidin-4-ylideneamine;
3-(3,4-dichloro-benzenesulfonyl)-2-methylsulfanyl-pyrido[1,2-a]pyrimidin-4-ylideneamine;
N-(3-benzenesulfonyl-2-methylsulfanyl-pyrido[1,2-a]pyrimidin-4-ylidene)methylamine;
3-(2-chloro-benzenesulfonyl)-2-methylsulfanyl-pyrido[1,2-a]pyrimidin-4-ylideneamine;
3-benzenesulfonyl-2-methylsulfanyl-pyrido[1,2-a]pyrimidin-4-ylideneamine;
3-(4-fluoro-benzenesulfonyl)-2-methylsulfanyl-pyrido[1,2-a]pyrimidin-4-ylideneamine;
2-(3-benzenesulfonyl-4-imino-4H-pyrido[1,2-a]pyrimidin-2-ylamino)ethanol;
3-benzenesulfonyl-2-methanesulfinyl-pyrido[1,2-a]pyrimidin-4-ylideneamine;
3-benzenesulfonyl-7-chloro-2-methylsulfanyl-pyrido[1,2-a]pyrimidin-4-ylideneamine;
3-(4-chloro-benzenesulfonyl)-2-methylsulfanyl-pyrido[1,2-a]pyrimidin-4-ylideneamine;
3-benzenesulfonyl-7-fluoro-2-methylsulfanyl-pyrido[1,2-a]pyrimidin-4-ylideneamine;
3-benzenesulfonyl-9-methyl-2-methylsulfanyl-pyrido[1,2-a]pyrimidin-4-ylideneamine;
3-benzenesulfonyl-9-benzyloxy-2-methylsulfanyl-pyrido[1,2-a]pyrimidin-4-ylideneamine;
3-benzenesulfonyl-8-methyl-2-methylsulfanyl-pyrido[1,2-a]pyrimidin-4-ylideneamine;
3-benzenesulfonyl-7-bromo-2-methylsulfanyl-pyrido[1,2-a]pyrimidin-4-ylideneamine;
2-methylsulfanyl-3-(4-trifluoromethoxy-benzenesulfonyl)-pyrido[1,2-a]pyrimidin-4-ylideneamine;
3-benzenesulfonyl-4-imino-2-methylsulfanyl-4H-pyrido[1,2-a]pyrimidine-7-carboxylic acid methyl ester;
3-benzenesulfonyl-2-methylsulfanyl-pyrimido[2,1-a]isoquinolin-4-ylideneamine;
3-(4-chloro-2,5-dimethyl-benzenesulfonyl)-2-methylsulfanyl-pyrido[1,2-a]pyrimidin-4-ylideneamine;
3-benzenesulfonyl-2-methylsulfanyl-pyrido[1,2-a]pyrimidin-4-one;
7-benzenesulfonyl-6-methylsulfanyl-4,5,8a-triazaphenanthren-8-ylideneamine;
2-methylsulfanyl-3-(naphthalene-2-sulfonyl)-pyrido[1,2-a]pyrimidin-4-ylideneamine;
3-benzenesulfonyl-7-benzyl-9-methyl-2-methylsulfanyl-pyrido[1,2-a]pyrimidin-4-ylideneamine;
(3-benzenesulfonyl-4-imino-7-methyl-4H-pyrido[1,2-a]pyrimidin-2-yl)-(5-methyl-pyridin-2-yl)amine;
3-(4-tert-butyl-benzenesulfonyl)-2-methylsulfanyl-pyrido[1,2-a]pyrimidin-4-ylideneamine;
3-benzenesulfonyl-2-methylsulfanyl-8-propyl-pyrido[1,2-a]pyrimidin-4-ylideneamine;
N-(3-benzenesulfonyl-2-methylsulfanyl-pyrido[1,2-a]pyrimidin-4-ylidene)acetamide;
3-benzenesulfonyl-4-imino-2-methylsulfanyl-4H-pyrido[1,2-a]pyrimidine-7-carboxylic acid amide; and
3-benzenesulfonyl-8-ethyl-2-methylsulfanyl-pyrido[1,2-a]pyrimidin-4-ylideneamine.

Biological Data

Radioligand Binding at the 5-$HT_6$ Receptor

Compounds of the present invention were evaluated using a cell line that stably expresses the human 5-$HT_6$ receptor. Membranes prepared from the cell line were incubated with 3H-LSD (1.6 nM) in the presence of increasing concentrations ($10^{-10}$ to $10^{-6}$ M) of test compounds for 60 minutes at 37° C. The reaction was terminated by vacuum filtration of the membranes and washing of the filters with assay buffer. Radioactivity retained on the filters was determined using liquid scintillation spectrometry. The potency of the test compound to inhibit 3H-LSD binding to the 5-$HT_6$ receptor was defined as the concentration of compound required to inhibit 50% ($IC_{50}$) of radioligand binding as determined by computer assisted analysis of the data. Clozapine was used as an internal standard for comparison. The data is summarized as Table I below.

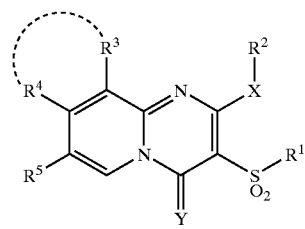

| Ex. | X | Y | $R^1$ | $R^2$ | $R^3$ | $R^4$ | $R^5$ | $IC_{50}$ (nM) |
|---|---|---|---|---|---|---|---|---|
| 1 | S | NH | Ph—Cl | $CH_3$ | H | H | H | + |
| 2 | S | NH | Ph | $CH_3$ | H | H | H | + |
| 3 | S | NH | Naphth | $CH_3$ | H | H | H | ++ |
| 4 | S | NH | $Ph(CH_3)_2Cl$ | $CH_3$ | H | H | H | + |
| 5 | S | NH | Ph—F | $CH_3$ | H | H | H | + |
| 6 | S | NH | $Ph(Cl)_2$ | $CH_3$ | H | H | H | + |
| 7 | S | NH | Ph—Cl | $CH_3$ | H | H | H | + |
| 8 | S | NH | Ph—t-bu | $CH_3$ | H | H | H | ++ |
| 9 | S | NH | Ph—$(OCF_3)$ | $CH_3$ | H | H | H | +++ |
| 10 | S | NH | Ph | $CH_3$ | $CH_3$ | H | H | + |
| 11 | S | NH | Ph | $CH_3$ | H | $CH_3$ | H | + |
| 12 | S | NH | Ph | $CH_3$ | H | H | Br | + |
| 13 | S | NH | Ph | $CH_3$ | H | H | Cl | + |
| 14 | S | NH | Ph | $CH_3$ | H | H | $CH_3$ | + |
| 15 | S | NH | Ph | $CH_3$ | Br | H | $CH_3$ | +++ |
| 16 | S | NH | Ph | $CH_3$ | $CH_3$ | H | Br | + |
| 17 | S | NH | Ph | $CH_3$ | H | Et | H | ++ |
| 18 | S | NH | Ph | $CH_3$ | H | Propyl | H | +++ |
| 19 | S | NH | Ph | $CH_3$ | H | H | $CO_2CH_3$ | +++ |
| 20 | S | NH | Ph | $CH_3$ | $CH_3$ | H | $CH_2$—Ph | ++ |
| 21 | S | NH | Ph | $CH_3$ | H | H | F | + |
| 22 | S | NH | Ph | $CH_3$ | $OCH_2Ph$ | H | H | +++ |
| 23 | S | NH | Ph | $CH_3$ | —CH=CH—CH=CH— | | H | ++ |
| 24 | S | NH | Ph | $CH_3$ | —N=CH—CH=CH— | | H | ++ |
| 25 | S | NH | Ph | $CH_3$ | H | H | $C(O)NH_2$ | + |
| 26 | NH | NH | Ph | $CH_3$ | H | H | H | + |
| 27 | NH | NH | Ph | Et | H | H | H | + |
| 28 | NH | NH | Ph | Pyr-Me | H | H | $CH_3$ | ++ |
| 29 | NH | NH | Ph | EtOH | H | H | H | + |
| 30 | O | NH | Ph | $CH_3$ | H | H | H | + |
| 31 | O | NH | Ph | Et | H | H | H | + |
| 32 | SO | NH | Ph | $CH_3$ | H | H | H | +++ |
| 33 | S | NMe | Ph | $CH_3$ | H | H | H | +++ |
| 34 | S | NAc | Ph | $CH_3$ | H | H | H | ++ |
| 35 | S | O | Ph | $CH_3$ | H | H | H | ++ |

+ = <20 nM; ++ = 50–100 nM; +++ = ± 100–1000 nM
Ph = phenyl, napth = naphthyl, pyr = pyridiyl, Et = ethyl Functional Assay of the 5-$HT_6$ Receptor The $5HT_6$ receptor responds to serotonin and other agonists by increasing adenyl cyclase mediated production of cyclic AMP (cAMP). Particular test compounds were assayed for their effect on adenyl cyclase activity using the procedure described below. Compounds acting as antagonists at the $5HT_6$ receptor will antagonize the agonist effect of serotonin and thus, will block the serotonin-induced increase in adenyl cyclase activity.

HeLa cells stably expressing the human $5HT_6$ receptor were plated in 96 well plates in UltraCULTURE™ serum-free media (BioWhittaker catalog #12-725F) and incubated overnight at 37° C. in a $CO_2$ incubator.

After overnight incubation, the serum-free media was removed from the wells (approximately 100% confluent) and 90 μl of RPMI-1640 media (without phenol red), supplemented with 20 mM HEPES and 100 μM IBMX, were added separately to each well in duplicate with one of a) serotonin (final concentrations 1 nM, 10 nM, 100 nM, 1 μM and 10 μM); b) test compound (1 nM, 10 nM, 100 nM, 1 μM and 10 μM, to test for agonist activity); and c) test compound (1 nM, 10 nM, 100 nM, 1 μM and 10 μM) along with serotonin (200 nM final concentration, to test for antagonist activity). Basal wells contained RPMI-1640 media with HEPES and IBMX. As compounds were initially dissolved in DMSO, the final concentration of DMSO in the assay is 1%.

The cells were incubated at 37° C. for 20 minutes in a $CO_2$ incubator. Following incubation, the media was removed from each well and 50 μl Lysis Reagent 1 (from Amersham cAMP SPA direct screening assay system; RPA 559) were added to each well. The plates were then placed on a plate shaker for 10 minutes (500 rpm) to enhance cell lysis. To each well of the cell plate was added 150 μl of immuno-reagent (1:1:1, Tracer, Antiserum, SPA reagent/fluomicrospheres from the Amersham SPA kit). On a separate plate, 50 μl of cAMP standard (serially diluted to provide a concentration range of 0.2 to 25.6 pmol) was added to each well in duplicate to prepare a standard plate and 150 μl of immuno-reagent was added to each of these wells. The cell and standard plates were then sealed and incubated for 15–20 hours at ambient temperature.

Incubation wells were counted for two minutes using a Wallac Trilux Microbeta counter and counts per minute (CPM) determined. Results from the standard plate were used to plot a linear cAMP standard curve and used for calculation of cAMP accumulation (pmol) in each well containing cells.

Certain compounds of Formula I were found to be antagonists of the 5-HT$_6$ receptor.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard conventional techniques.

The pharmaceutical compositions include suitable dosage forms for oral, parenteral (including subcutaneous, intramuscular, intradermal, and intravenous), transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents, and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions, and the like, may be utilized. Injectable suspensions also may be used, in which case conventional suspending agents may be employed. Conventional preservatives, buffering agents and the like also may be added to the parenteral dosage forms. Particularly useful is the administration of a compound of Formula I in oral dosage formulations. The pharmaceutical compositions are prepared by conventional techniques appropriate to the desired preparation containing appropriate amounts of the active ingredient, that is, the compound of Formula I according to the invention. See for example, *Remington's Pharmaceutical Sciences*, Mack Publishing Company, Easton, Pa., 17$^{th}$ edition, 1985.

In making pharmaceutical compositions containing compounds of the present invention, the active ingredient(s) will usually be mixed with a carrier, diluted by a carrier, or enclosed within a carrier which may be in the form of a capsule, sachet, paper or other container. When the carrier serves as a diluent, it may be a solid, semi-solid, or liquid material which acts as a vehicle, excipient, or medium for the active ingredient. Thus, the composition can be in the form of tablets, pills, powders, lozenges, sachets, cachets, elixirs, suspensions, emulsions, solutions, syrups, aerosols (as a solid or a liquid medium), ointments, soft and hard gelatin capsules, suppositories, sterile injectable solutions, and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate, and mineral oil. The formulations can additionally include lubricating agents, wetting agents, emulsifying and suspending agents, preserving agents, sweetening agents, or flavoring agents. The compositions of the invention may be formulated so as to provide quick, sustained or delayed release of the active ingredient after administration to the patient.

The dosage of the compounds of Formula I to achieve a therapeutic effect will depend not only on such factors as the age, weight and sex of the patient, and mode of administration, but also on the degree of serotonergic activity desired and the potency of the particular compound being utilized for the particular disorder or condition concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of a physician, and may be varied by titration of the dosage to the particular circumstances of this invention to produce the desired therapeutic effect.

The compositions are preferably formulated in a unit dosage form. The term "unit dosage form" refers to physically discrete units suitable as unitary dosages for human subjects and other mammals, each unit containing a predetermined quantity of active material calculated to produce the desired therapeutic effect, in association with the required pharmaceutical carrier. These active compounds are effective over a wide dosage range. For example, dosages per day will normally fall within the range of about 0.05 to about 500 mg. In the treatment of adult humans, the range of about 0.1 to about 10 mg/day, in single or divided doses, is preferred. Generally, the compounds of the invention may be used in treating central nervous system disorders which implicate the 5-HT$_6$ receptor. Such disorders include psychoses, schizophrenia, manic depression, depression, neurological disorders, memory disorders, cognition enhancement, Parkinson's disease, amyotrophic lateral sclerosis, Alzheimer's disease, and Huntington's chorea.

However, it will be understood that the amount of the compound actually administered will be determined by a physician, in light of the relevant circumstances including the condition to be treated, the choice of compound to be administered, the chosen route of administration, the age, weight and response of the individual patient, and the severity of the patient's symptoms.

The compounds which constitute this invention, their methods of preparation and their biologic actions will appear more fully from consideration of the following examples, which are given for the purpose of illustration only and are not to be construed as limiting the invention in sphere or scope.

DESCRIPTION OF SPECIFIC EMBODIMENTS

In the following examples, used to illustrate the foregoing synthetic processes, proton magnetic resonance ($^1$H NMR) spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet quartet.

Preparation of Intermediate 1

2-Benzenesulfonyl-3,3-bis-methylsulfanyl-acrylic acid methyl ester

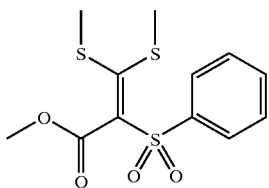

Methyl phenylsulfonylacetate (5 g, 23.3 mmol) was mixed with carbon disulfide (1.77 g, 23.3 mmol) in anhydrous DMSO (100 ml) at room temperature. Sodium hydride (60% in mineral oil, 1.2 g, 48.9 mmol) was added portionwise. After stirring at room temperature for 1 hour, iodomethane (6.9 g, 48.9 mmol) was added neat and the reaction mixture was stirred overnight. The reaction mixture was quenched by the addition of water, and the resulting mixture extracted with dichloromethane. The organic layer was purified via flash chromatography and concentrated in vacuo to provide crude 2-benzenesulfonyl-3,3-bis-methylsulfanyl-acrylic acid methyl ester, which was further purified by recrystallization from methanol to yield 3.7 grams of white solid. $^1$H NMR (500 MHz, CDCl$_3$): δ 8.1 (d, 2H), 7.6 (t, 1H), 7.5 (t, 2H), 3.9 (s, 3H), 2.4 (s, 3H), 2.2 (s, 3H).

Preparation of Intermediate 2

2-(4-Chlorobenzenesulfonyl)-3,3-bis-methylsulfanyl-acrylonitrile

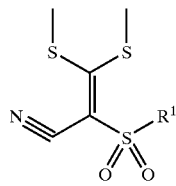

To a solution of 2-(4-chlorobenzenesulfonyl) acetonitrile (600 mg, 2.78 mmol) in anhydrous DMSO (8 ml) under an argon atmosphere was added carbon disulfide (212 mg, 2.78 mmol). The reaction mixture was cooled to approximately 0° C. and 2 equivalents of sodium hydride (5.56 mmol) was added in one portion. The resulting thick reaction mixture was swirled until homogeneous and allowed to warm to room temperature for one hour with stirring. The reaction mixture was cooled again to 0° C. and 2 equivalents of iodomethane (5.56 mmol) was added under argon. The reaction mixture was allowed to gradually warm to room temperature and after 18 hours deionized water was added (30 ml) and the resulting slurry was stirred for 15 minutes. The solid was collected by filtration, washed with deionized water, and dried. The crude solid product thus obtained was dissolved in 25% hexanes/chloroform and purified via flash chromatography. The resulting solution was concentrated in vacuo to provide the titled compound as a light yellow solid in 65% yield.

$^1$H NMR (300 MHz, CDCl$_3$): δ 8.0–7.9 (d, 2H), 7.6–7.5 (d, 2H), 2.7 (s, 3H), 2.6 (s, 3H).

Preparation of Intermediate 3

2-Benzenesulfonyl-3,3-bis-methylsulfanyl-acrylonitrile

The titled compound was prepared in an analogous fashion to Intermediate 2 starting from 2-(benzenesulfonyl) acetonitrile in place of 2-(4-chlorobenzenesulfonyl) acetonitrile.

$^1$H NMR (300 MHz, CDCl$_3$): δ 8.0 (d, 2H), 7.6 (t, 1H), 7.5 (t, 2H), 2.7 (s, 3H), 2.6 (s, 3H).

Preparation of Intermediate 4

3,3-Bis-methylsulfonyl-2-(naphthalene-2-sulfonyl)-acrylonitrile

The titled compound was prepared in an analogous fashion to Intermediate 2 starting from 2-(napthalene-2-ylsulfonyl) acetonitrile in place of 2-(4-chlorobenzenesulfonyl) acetonitrile.

$^1$H NMR (300 MHz, CDCl$_3$): δ 8.6 (s, 1H), 8.0–7.9 (m, 4H), 7.7–7.6 (m, 2H), 2.7 (s, 3H), 2.6 (s, 3H).

Preparation of Intermediate 5

2-(4-Chloro-2,5-dimethyl-benzenesulfonyl)-3,3-bis-methylsulfonyl-acrylonitrile

The titled compound was prepared in an analogous fashion to Intermediate 2 except that 2-(2,5-dimethyl-4-chlorobenzenesulfonyl) acetonitrile was utilized in place of 2-(4-chlorobenzenesulfonyl) acetonitrile.

$^1$H NMR (300 MHz, CDCl$_3$): δ 8.0 (s, 1H), 7.3 (s, 1H), 7.2 (s, 1H), 2.7 (s, 3H), 2.6 (s, 3H), 2.5 (s, 3H), 2.4 (s, 3H).

Preparation of Intermediate 6

2-(4-Fluoro-benzenesulfonyl)-3,3-bis-methylsulfonyl-acrylonitrile

The titled compound was prepared in an analogous fashion to Intermediate 2 except that 2-(4-fluoro-benzenesulfonyl) acetonitrile is utilized in place of 2-(4-chlorobenzenesulfonyl) acetonitrile.

$^1$H NMR (300 MHz, CDCl$_3$): δ 8.0 (m, 2H), 7.2 (m, 2H), 2.7 (s, 3H), 2.6 (s, 3H).

Preparation of Intermediate 7

2-(3,4-Dichloro-benzenesulfonyl)-3,3-bis-methylsulfonyl-acrylonitrile

The titled compound was prepared in an analogous fashion to Intermediate 2 except that 2-(3,5-dichlorobenzenesulfonyl) acetonitrile is utilized in place of 2-(4-chlorobenzenesulfonyl) acetonitrile.

$^1$H NMR (CDCl$_3$): δ 8.1 (s, 1H), 7.9 (d, 1H), 7.6 (d, 1H), 2.7 (s, 3H), 2.6 (s, 3H).

Preparation of Intermediate 8

2-(2-Chloro-benzenesulfonyl)-3,3-bis-methylsulfonyl-acrylonitrile

The titled compound was prepared in an analogous fashion to Intermediate 2 except that 2-(2-chlorobenzenesulfonyl) acetonitrile is utilized in place of 2-(4-chlorobenzenesulfonyl) acetonitrile.

$^1$H NMR (CDCl$_3$): δ 8.3 (d, 1H), 7.6–7.4 (m, 3H), 2.7 (s, 3H), 2.4 (s, 3H).

Preparation of Intermediate 9

2-(4-t-Butyl-benzenesulfonyl)-3,3-bis-methylsulfonyl-acrylonitrile

The titled compound was prepared in an analogous fashion to Intermediate 2 except that 2-(4-tertbutylbenzenesulfonyl) acetonitrile is utilized in place of 2-(4-chlorobenzenesulfonyl) acetonitrile.

$^1$H NMR (CDCl$_3$): δ 8.0 (d, 2H), 7.6 (d, 2H), 2.7 (s, 3H), 2.6 (s, 3H), 1.4 (s, 9H).

Preparation of Intermediate 10

2-(4-Trifluoromethoxybenzenesulfonyl)-3,3-bis-methylsulfonyl-acrylonitrile

The titled compound was prepared in an analogous fashion to Intermediate 2 except that 2-(2-chlorobenzenesulfonyl) acetonitrile is utilized in place of 2-(4-chlorobenzenesulfonyl) acetonitrile.

$^1$H NMR (CDCl$_3$): δ 8.1 (d, 2H), 7.4 (d, 2H), 2.7 (s, 3H), 2.6 (s, 3H).

EXAMPLES

Examples 1 through 25 of Formula I were prepared according to Methods A–D described below.

Method A: In one dram vial fitted with a TEFLON® lined cap, substituted 2-aminopyridine (0.12 mmol) was dissolved or suspended in 200 ul of dioxane at room temperature and sodium bis(trimethylsilyl)amide (120 ul in THF, 0.12 mmol) was added. After 15 minutes, 2-benzenesulfonyl-3,3-bis-methylsulfanyl-acrylonitrile in dioxane (120 ul, 0.12 mmol) was added to the reaction vial, which was then subjected to heating at 80° C. in a metal heating block with shaking overnight. The reaction mixture was concentrated, diluted by CH$_2$Cl$_2$, and washed with aqueous NH$_4$Cl. The organic layer was concentrated in vacuo; the residue was then taken up in a DMF/MeOH mixture (1:1) and subjected to reverse phase preparative HPLC (XTerra™ MS C18 5.0 mM) using MeOH/H$_2$O mixture as the eluent. Product was collected after fractions were concentrated in vacuo.

Method B: In one dram vial fitted with a TEFLON® lined cap, substituted 2-aminopyridine (0.6 mmol) was dissolved in 400 ul DMF at room temperature and 2-benzenesulfonyl-3,3-bis-methylsulfanyl-acrylonitrile in dimethylformamide (120 ul, 0.12 mmol) was added. The reaction mixture was subjected to heating at 80° C. in a metal heating block with shaking overnight. After cooling to room temperature, the reaction mixture was further diluted with DMF and/or MeOH and subjected directly to reverse phase preparative HPLC using TFA (trifluoroacetic acid, 0.1%) buffered MeOH/H$_2$O mixture as the eluent. Product was collected after fractions were concentrated in vacuo.

Method C: Same as in method B except that the reaction was carried out in anhydrous ethanol.

Method D: To a one dram vial was added 20 mg of 2-arylsulfonyl-3,3-bis-methylsulfanyl-acrylonitrile along with 2 equivalents of 2-aminopyridine in 750 ul of DMF. The vial was fitted with a TEFLON® lined cap and heated to 80° C. in a sand bath for 2 days. The crude product was allowed to return to room temperature, diluted to 2 ml with methanol or acetonitrile and purified on a reverse phase preparative HPLC column (XTerra™ MS C18 5.0 mM, MeOH/H$_2$O as the eluent) to give the title compound.

Example 1

3-(4-Chloro-benzenesulfonyl)-2-methylsulfanyl-pyrido[1,2-a]pyrimidin-4-ylideneamine

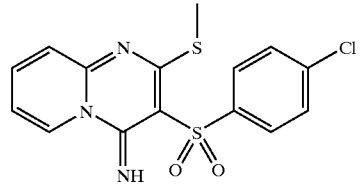

The title compound was prepared by method D. $^1$H NMR (CDCl$_3$): δ 9.7 (d, 1H), 8.2 (t, 1H), 8.0 (d, 2H), 7.8 (d, 1H), 7.7 (t, 1H), 7.5 (d, 2H), 2.6 (s, 3H).

Example 2

3-Benzenesulfonyl-2-methylsulfanyl-pyrido[1,2-a]pyrimidin-4-ylideneamine

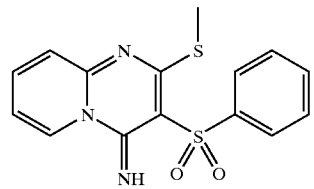

The title compound was prepared by method C. $^1$H NMR (300 MHz, CDCl$_3$): δ 9.43–9.41 (1H, brd), 8.09–8.06 (2H, m), 7.80–7.75 (1H, m), 7.58–7.56 (1H, m), 7.51–7.46 (2H, m), 7.37–7.34 (1H, m), 7.26 (1H, s), 7.08–7.04 (1H, m), 2.49 (3H, s).

Example 3

2-Methylsulfanyl-3-(naphthalene-2-sulfonyl)-pyrido[2-a]pyrimidin-4-ylideneamine

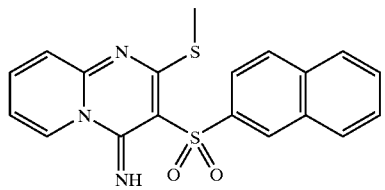

The title compound was prepared by method D. $^1$H NMR (CDCl$_3$): δ 9.6 (d, 1H), 8.6 (s, br, 1H), 8.0 (d, 2H), 7.9 (s, 1H), 7.8 (m, 4H), 7.4 (d, 2H), 7.1 (t, 1H), 2.5 (s, 3H).

Example 4

3-(2,5-Dimethyl-4-Chloro-benzenesulfonyl)-2-methylsulfanyl-pyrido[1,2-a]pyrimidin-4-ylideneamine

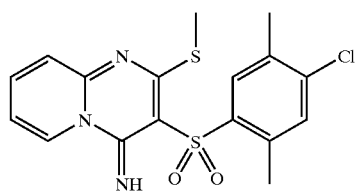

The title compound was prepared by method D. $^1$H NMR (CDCl$_3$): δ 9.5 (d, 1H), 8.1 (s, br, 1H), 7.8 (t, 1H), 7.4 (d, 1H), 7.2 (d, 2H), 7.1 (t, 1H), 2.5 (s, 3H), 2.4 (s, 6H).

Example 5

3-(4-Fluoro-benzenesulfonyl)-2-methylsulfanyl-pyrido[1,2-a]pyrimidin-4-ylideneamine

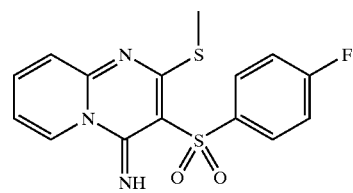

The title compound was prepared by method D. $^1$H NMR (CDCl$_3$): δ 9.4 (d, 1H), 9.0 (s, br, 1H), 8.1 (m, 2H), 7.8 (t, 1H), 7.3 (d, 1H), 7.2 (t, 2H), 7.1 (t, 1H), 2.5 (s, 3H).

Example 6

3-(3,4-Dichloro-benzenesulfonyl)-2-methylsulfanyl-pyrido[1,2-a]pyrimidin-4-ylideneamine

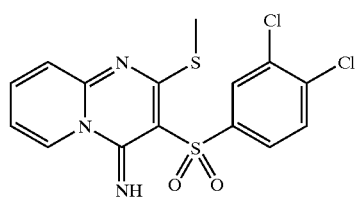

The title compound was prepared by method D. $^1$H NMR (CDCl$_3$): δ 9.6 (d, 1H), 8.1 (s, 1H), 7.9–7.8 (m, 3H), 7.6 (d, 1H), 7.4 (d, 1H), 7.1 (t, 1H), 2.5 (s, 3H).

Example 7

3-(2-Chloro-benzenesulfonyl)-2-methylsulfanyl-pyrido[1,2-a]pyrimidin-4-ylideneamine

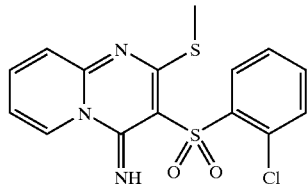

The title compound was prepared by method D. $^1$H NMR (CDCl$_3$): δ 9.4 (d, 1H), 9.1 (s, 1H), 8.4 (d, 1H), 7.8 (t, 1H), 7.5 (t, 3H), 7.3 (d, 1H), 7.0 (t, 1H), 2.4 (s, 3H).

Example 8

3-(4-t-Butyl-benzenesulfonyl)-2-methylsulfanyl-pyrido[1,2-a]pyrimidin-4-ylideneamine

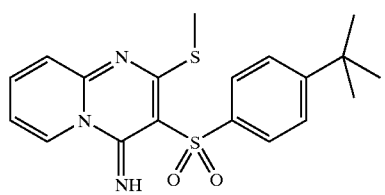

The title compound was prepared by method D. $^1$H NMR (CDCl$_3$): δ 9.4 (d, 1H), 9.1 (s, br, 1H), 8.0 (d, 2H), 7.7 (t, 1H), 7.5 (d, 2H), 7.3 (d, 1H), 7.0 (t, 1H), 2.5 (s, 3H), 1.3 (s, 9H).

Example 9

3-(4-Trifluoromethoxy-benzenesulfonyl)-2-methylsulfanyl-pyrido[1,2-a]pyrimidin-4-ylideneamine

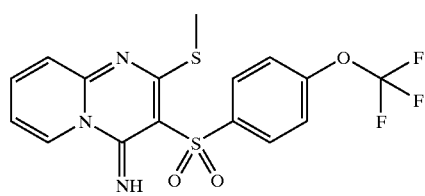

The title compound was prepared by method D. $^1$H NMR (CDCl$_3$): δ 9.3 (d, 1H), 9.0 (s, br, 1H), 8.1 (d, 2H), 7.7 (t, 1H), 7.2 (d, 1H), 7.3 (d, 2H), 7.0 (t, 1H), 2.4 (s, 3H).

Example 10

3-Benzenesulfonyl-9-methyl-2-methylsulfanyl-pyrido[1,2-a]pyrimidin-4-ylideneamine

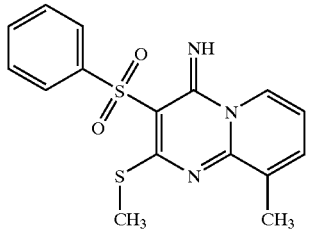

The title compound was prepared by method A. $^1$H NMR (500 MHz, CDCl$_3$): δ 9.27 (1H, d, 6.4 Hz), 9.05 (1H, s), 8.09 (2H, dd, 8.3 Hz, 1.0 Hz), 7.64 (1H, d, 7.0 Hz), 7.58 (1H, t, 7.6 Hz), 7.49 (2H, t, 7.6 Hz), 6.96 (1H, t, 7.0 Hz), 2.51 (3H, s), 2.46 (3H, s).

Example 11

3-Benzenesulfonyl-8-methyl-2-methylsulfanyl-pyrido[1,2-a]pyrimidin-4-ylideneamine

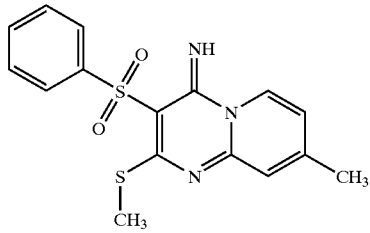

The title compound was prepared by method A. $^1$H NMR (500 MHz, CDCl$_3$): δ 9.26 (1H, d, 7.3 Hz), 9.02 (1H, br, s), 8.07 (2H, dd, 8.3 Hz, 1.0 Hz), 7.57 (1H, t, 7.3 Hz), 7.48 (2H, m), 7.15 (1H, s), 6.88 (1H, dd, 7.3 Hz, 1.8 Hz), 2.48 (3H, s), 2.44 (3H, s).

The title compound was prepared by method B. Mono TFA salt: $^1$H NMR (500 MHz, CDCl$_3$): δ 9.42 (1H, d, 6.7 Hz), 8.08 (2H, d, 7.3 Hz), 7.70 (1H, t, 7.6 Hz), 7.52–7.62 (4H, m), 2.62 (3H, s), 2.60 (3H, s).

Example 12

3-Benzenesulfonyl-7-bromo-2-methylsulfanyl-pyrido[1,2-a]pyrimidin-4-ylideneamine

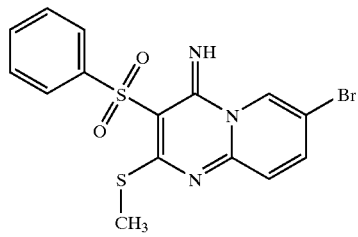

The title compound was prepared by method A. $^1$H NMR (500 MHz, CDCl$_3$): δ 9.50 (1H, d, 2.2 Hz), 9.11 (1H, br, s), 8.06 (2H, dd, 8.3 Hz, 1.0 Hz), 7.77 (1H, dd, 9.3 Hz, 2.2 Hz), 7.59 (1H, t, 7.3 Hz), 7.49 (2H, m), 7.21 (1H, d, 9.3 Hz), 2.48 (3H, s).

The mono TFA salt was prepared by method B. Mono TFA salt: $^1$H NMR (500 MHz, CDCl$_3$) δ 9.64 (1H, s), 8.08 (2H, d, 7.6 Hz), 8.05 (1H, d, 9.4 Hz), 7.69 (1H, t, 7.6 Hz), 7.56 (2H, t, 7.6 Hz), 7.53 (1H, d, 9.2 Hz), 2.59 (3H, s).

Example 13

3-Benzenesulfonyl-7-chloro-2-methylsulfanyl-pyrido[1,2-a]pyrimidin-4-ylideneamine

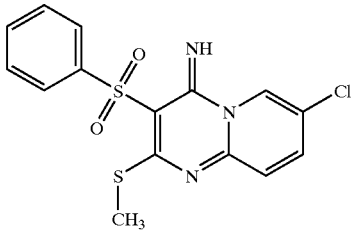

The title compound was prepared by method A. $^1$H NMR (500 MHz, CDCl$_3$): δ 9.41 (1H, d, 2.4 Hz), 9.13 (1H, br, s), 8.06 (2H, dd, 8.3 Hz, 1.0 Hz), 7.67 (1H, dd, 9.5 Hz, 2.4 Hz), 7.60 (1H, t, 7.3 Hz), 7.49 (2H, t, 7.6 Hz), 7.28 (1H, d, 9.5 Hz), 2.49 (3H, s).

The mono TFA salt was prepared by method B. Mono TFA salt: $^1$H NMR (500 MHz, CDCl$_3$): δ 9.56 (1H, s), 8.06 (2H, d, 7.3 Hz), 7.91 (1H, dd, 9.5 Hz, 1.8 Hz), 7.67 (1H, t, 7.6 Hz), 7.52–7.58 (3H, m), 2.57 (3H, s).

Example 14

3-Benzenesulfonyl-7-methyl-2-methylsulfanyl-pyrido[1,2-a]pyrimidin-4-ylideneamine

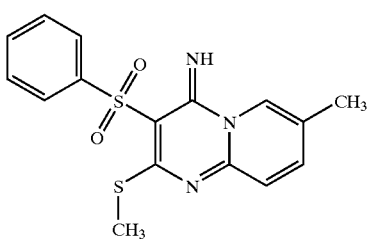

The title compound was prepared by method A. $^1$H NMR (500 MHz, CDCl$_3$): δ 9.19 (1H, s), 9.04 (1H, br, s), 8.07 (2H, dd, 8.3 Hz, 1.0 Hz), 7.63 (1H, dd, 9.0 Hz, 2.0 Hz), 7.57 (1H, t, 7.3 Hz), 7.48 (2H, t, 7.6 Hz), 7.29 (1H, d, 8.9 Hz), 2.49 (3H, s), 2.37 (3H, s).

The mono TFA salt was prepared by method B. Mono TFA salt: $^1$H NMR (500 MHz, CDCl$_3$): δ 9.25 (1H, s), 8.09 (2H, d, 7.6 Hz), 7.99 (1H, d, 9.1 Hz), 7.71 (1H, d, 8.9 Hz), 7.70 (1H, t, 7.0 Hz), 7.57 (2H, t, 7.6 Hz), 2.60 (3H, s), 2.55 (3H, s).

Example 15

3-Benzenesulfonyl-9-bromo-7-methyl-2-methylsulfanyl-pyrido[1,2-a]pyrimidin-4-ylideneamine

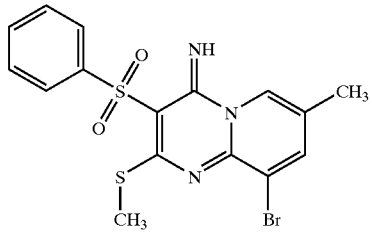

The title compound was prepared by method A. $^1$H NMR (500 MHz, CDCl$_3$): δ 9.17 (1H, s), 9.12 (1H, s), 8.06 (2H, dd, 8.3 Hz, 1.2 Hz), 7.98 (1H, d, 1.8 Hz), 7.58 (1H, t, 7.6 Hz), 7.48 (2H, t, 7.6 Hz), 2.57 (3H, s), 2.35 (3H, s).

Example 16

3-Benzenesulfonyl-7-bromo-9-methyl-2-methylsulfanyl-pyrido[1,2-a]pyrimidin-4-ylideneamine

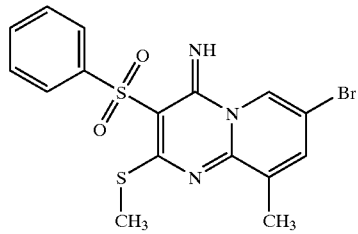

The title compound was prepared by method A. $^1$H NMR (500 MHz, CDCl$_3$): δ 9.40 (1H, d, 1.8 Hz), 9.08 (1H, s), 8.06 (2H, dd, 8.3 Hz, 1.0 Hz), 7.68 (1H, d, 2.1 Hz), 7.59 (1H, t, 7.6 Hz), 7.49 (2H, t, 7.6 Hz), 2.50 (3H, s), 2.43 (3H, s).

Example 17

3-Benzenesulfonyl-8-ethyl-2-methylsulfanyl-pyrido[1,2-a]pyrimidin-4-ylideneamine

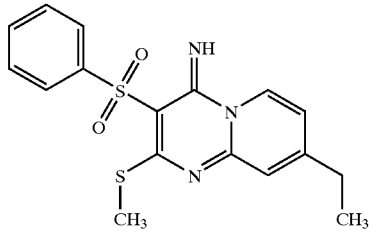

The title compound was prepared by method A. $^1$H NMR (500 MHz, CDCl$_3$): δ 9.27 (1H, d, 7.3 Hz), 9.02 (1H, br, s), 8.07 (2H, dd, 8.3 Hz, 1.3 Hz), 7.57 (1H, t, 7.6 Hz), 7.48 (2H, t, 7.6 Hz), 7.15 (1H, s), 6.91 (1H, dd, 7.3 Hz, 2.0 Hz), 2.73 (2H, q, 7.6 Hz), 2.49 (3H, s), 1.30 (3H, t, 7.6 Hz).

Example 18

3-Benzenesulfonyl-2-methylsulfanyl-8-propyl-pyrido[1,2-a]pyrimidin-4-ylideneamine

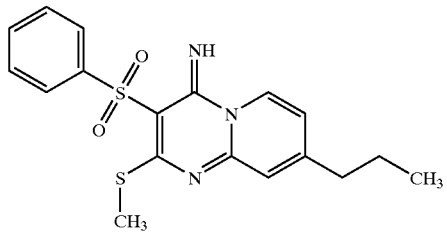

The title compound was prepared by method A. $^1$H NMR (500 MHz, CDCl$_3$): δ 9.27 (1H, d, 7.6 Hz), 9.02 (1H, br, s), 8.07 (2H, dd, 8.3 Hz, 1.0 Hz), 7.57 (1H, t, 7.6 Hz), 7.47 (2H, t, 7.6 Hz), 7.13 (1H, s), 6.89 (1H, dd, 7.3 Hz, 1.8 Hz), 2.66 (2H, t, 7.6 Hz), 2.49 (3H, s), 1.71 (2H, m), 0.98 (3H, t, 7.6 Hz).

Example 19

3-Benzenesulfonyl-4-imino-2-methylsulfanyl-4H-pyrido[1,2-a]pyrimidine-7-carboxylic acid methyl ester

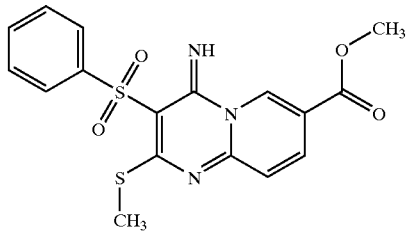

The title compound was prepared by method A. $^1$H NMR (500 MHz, CDCl$_3$): δ 9.97 (1H, d, 2.1 Hz), 9.28 (1H, s), 8.19 (1H, dd, 9.2 Hz, 1.5 Hz), 8.07 (2H, d, 7.9 Hz), 7.60 (1H, t, 7.6 Hz), 7.50 (2H, t, 7.6 Hz), 7.29 (1H, d, 9.2 Hz), 3.95 (3H, s), 2.50 (3H, s).

Example 20

3-Benzenesulfonyl-7-benzyl-9-methyl-2-methylsulfanyl-pyrido[1,2-a]pyrimidin-4-ylideneamine

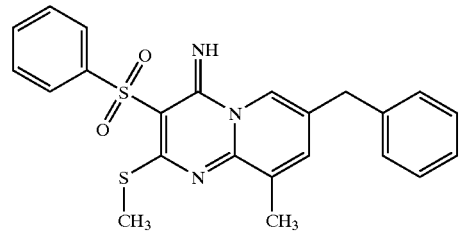

The title compound was prepared by method A. $^1$H NMR (500 MHz, CDCl$_3$): δ 9.19 (1H, s), 9.01 (1H, br, s), 8.09 (2H, dd, 8.3 Hz, 1.0 Hz), 7.57 (1H, t, 7.6 Hz), 7.48 (2H, t, 7.6 Hz), 7.43 (1H, s), 7.31 (2H, t, 7.6 Hz), 7.25 (1H, t, 7.3 Hz), 7.17 (2H, d, 7.6 Hz), 3.93 (2H, s), 2.49 (3H, s), 2.38 (3H, s).

Example 21

3-Benzenesulfonyl-7-fluoro-2-methylsulfanyl-pyrido[1,2-a]pyrimidin-4-ylideneamine

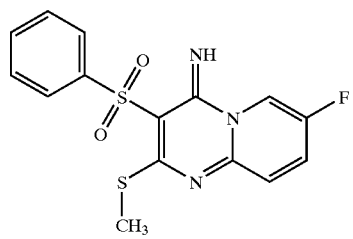

The title compound was prepared by method A. $^1$H NMR (500 MHz, CDCl$_3$): δ 9.33 (1H, dd, 5.2 Hz, 3.0 Hz), 9.11 (1H, s), 8.07 (2H, dd, 8.3 Hz, 1.0 Hz), 7.66 (1H, m), 7.59 (1H, t, 7.3 Hz), 7.49 (2H, t, 7.6 Hz), 7.35 (1H, dd, 9.5 Hz, 5.2 Hz), 2.48 (3H, s).

Example 22

3-Benzenesulfonyl-9-benzyloxy-2-methylsulfanyl-pyrido[1,2-a]pyrimidin-4-ylideneamine, mono TFA salt

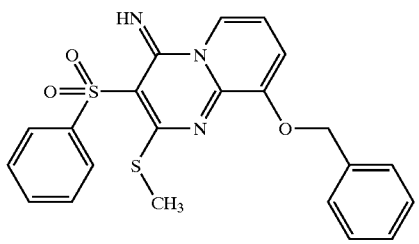

The title compound was prepared by method B. $^1$H NMR (500 MHz, CDCl$_3$): δ 9.14 (1H, d, 7.0 Hz), 8.11 (2H, d, 7.3 Hz), 7.71 (1H, t, 7.6 Hz), 7.58 (3H, m), 7.35–7.49 (6H, m), 5.30 (2H, s), 2.64 (3H, s).

Example 23

3-Benzenesulfonyl-2-methylsulfanyl-pyrimido[2,1-a]isoquinolin-4-ylideneamine, mono TFA salt

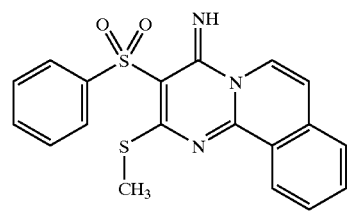

The title compound was prepared by method B. $^1$H NMR (500 MHz, CDCl$_3$): δ 9.14 (1H, d, 7.3 Hz), 9.00 (1H, d, 8.2 Hz), 8.14 (2H, d, 7.6 Hz), 8.05 (1H, t, 7.0 Hz), 7.94 (1H, d, 7.9 Hz), 7.89 (1H, t, 7.7 Hz), 7.85 (1H, d, 7.0 Hz), 7.72 (1H, t, 7.3 Hz), 7.59 (2H, t, 7.6 Hz), 2.82 (3H, s).

Example 24

7-Benzenesulfonyl-6-methylsulfanyl-4,5,8a-triazaphenanthren-8-ylideneamine, mono TFA salt

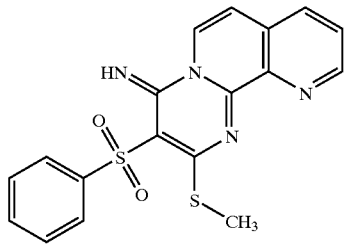

The title compound was prepared by method B. $^1$H NMR (500 MHz, CDCl$_3$): δ 9.81 (1H, d, 7.6 Hz), 9.22 (1H, dd, 4.6 Hz, 1.6 Hz), 8.26 (1H, dd, 8.2 Hz, 1.5 Hz), 8.13 (2H, dd, 8.5 Hz, 1.2 Hz), 7.91 (1H, dd, 8.2 Hz, 4.6 Hz), 7.83 (1H, d, 7.6 Hz), 7.73 (1H, t, 7.3 Hz), 7.59 (2H, t, 7.6 Hz), 2.90 (3H, s).

Example 25

3-Benzenesulfonyl-4-imino-2-methylsulfanyl-4H-pyrido[1,2-a]pyrimidine-7-carboxylic acid amide, mono TFA salt

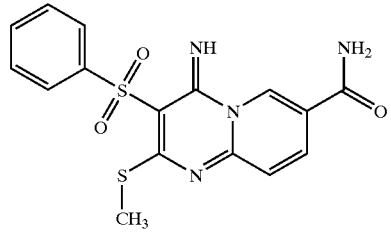

The title compound was prepared by method B. $^1$H NMR (500 MHz, CDCl$_3$): δ 9.96 (1H, s), 8.87 (1H, s), 8.71 (1H, dd, 9.1 Hz, 1.5 Hz), 8.11 (2H, dd, 8.2 Hz, 1.2 Hz), 7.81 (1H, d, 9.1 Hz), 7.74 (1H, t, 7.6 Hz), 7.61 (2H, m), 5.92 (1H, s), 2.66 (3H, s).

Example 26

3-Benzenesulfonyl-4-imino-4H-pyrido[1,2-a]pyrimidin-2-yl)-methyl-amine

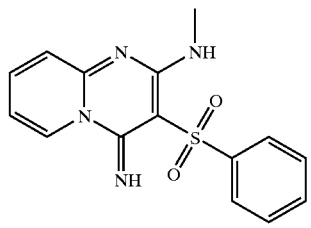

3-Benzenesulfonyl-2-methylsulfanyl-pyrido[1,2-a]pyrimidin-4-ylideneamine (100 mg, 0.30 mmol) was dissolved in DMF (2 ml). Methylamine (0.3 mmol, 2M in THF) was added at room temperature, followed immediately by addition of mercury (II) acetate (96 mg, 0.30 mmol) in one portion. After 10 minutes, the solvent was evaporated under a stream of nitrogen and the crude product was purified by preparative HPLC (XTerra™ MS C18 5.0 mM, MeOH/H₂O as the eluent). The product was obtained as a pale yellow solid, 26 mg.

¹H NMR (500 MHz, CDCl₃): δ 9.2 (d, 1H), 8.3 (s, br, 1H), 8.0 (s, br, 1H), 7.9 (d, 2H), 7.6–7.4 (m, 4H), 7.1 (d, 1H), 6.8 (t, 1H), 3.1 (d, 3H).

Example 27

3-(Benzenesulfonyl-4-imine-4H-pyrido[1,2-a]pyrimidin-2-yl)-ethyl-amine

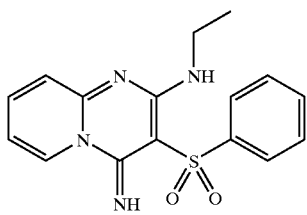

The title compound was prepared in an analogous fashion to Example 26 using ethylamine in place of methylamine.

¹H NMR (CDCl₃): δ 9.2 (d, 1H), 8.3 (s, br, 1H), 8.1 (s, br, 1H), 8.0 (d, 1H), 7.6–7.4 (m, 5H), 7.1 (d, 1H), 6.8 (t, 1H), 3.6 (m, 2H), 1.2 (t, 3H).

Example 28

3-Benzenesulfonyl-4-imino-7-methyl-4H-pyrido[1,2-a]pyrimidin-2-yl)-(5-methyl-pyridin-2-yl)-amine, mono TFA salt

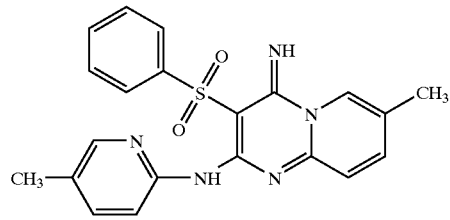

The title compound was produced as a minor product during the preparation, by method B, of 3-benzenesulfonyl-7-methyl-2-methylsulfanyl-pyrido[1,2-a]pyrimidin 4-ylideneamine, mono TFA salt (example 14). ¹H NMR (500 MHz, CDCl₃): δ 8.99 (1H, s), 8.35 (1H, s), 8.07 (2H, d, 7.6 Hz), 8.05 (1H, d, 8.5 Hz), 7.84 (1H, d, 9.1 Hz), 7.67–7.73 (2H, m), 7.57 (2H, t, 7.6 Hz), 7.52 (1H, d, 8.9 Hz), 2.46 (3H, s), 2.41 (3H, s).

Example 29

2-(3-Benzenesulfonyl-4-imino-4H-pyrido[1,2-a]pyrimidin-2-ylamino)-ethanol

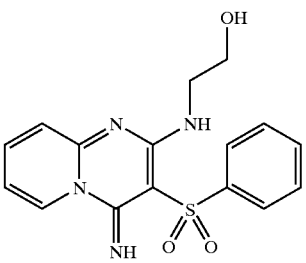

To a one dram vial was added 20 mg (0.0604 mmol) of 3-(benzenesulfonyl)-2-methylsulfanyl-pyrido[1,2-a]pyrimidin-4-ylideneamine and 1.1 equivalents of ethanolamine in 750 ml of DMF. The vial was fitted with a TEFLON® lined cap and heated to 55° C. over night. The resulting product was then purified on a reverse phase preparative HPLC (XTerra™ MS C18 5.0 mM, MeOH/H₂O as the eluent) to give 23 mg of the title compound as a brown solid; 10% yield.

¹H NMR: δ 9.3 (d, 1H), 8.5 (s, br, 2H), 8.0 (d, 2H), 7.7 (t, 1H), 7.6 (t, 1H), 7.5 (t, 2H), 7.2 (d, 1H), 6.9 (t, 1H), 3.9 (m, 2H), 3.8 (m, 2H).

Example 30

3-Benzenesulfonyl-2-methoxy-pyrido[1,2-a]pyrimidin-4-ylideneamine

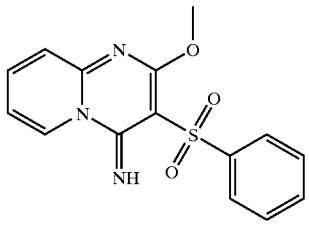

3-Benzenesulfonyl-2-methylsulfanyl-pyrido[1,2-a]pyrimidin-4-ylideneamine (50 mg, 0.15 mmol) was dissolved in methanol (2 ml) and heated at 90° C. for 4 days. When the conversion reached about 50% the product was isolated from the starting material by preparative HPLC (XTerra™ MS C18 5.0 mM, MeOH/H₂O as the eluent) to yield 21 mg of bright yellow product.

¹H NMR (300 MHz, CDCl₃): δ 9.55 (1H, d), 9.45 (1H, brs), 8.01–7.98 (2H, m), 7.83–7.77 (1H, m), 7.55–7.45 (3H, m), 7.30 (1H, d, J=8.8 Hz), 7.13–7.08 (1H, m), 3.89 (3H, s).

Example 31

3-Benzenesulfonyl-2-ethoxy-pyrido[1,2-a]
pyrimidin-4-ylideneamine, mono TFA salt

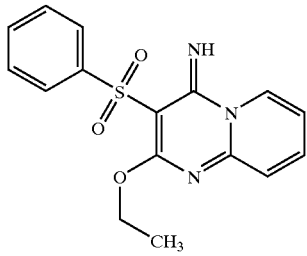

The title compound was produced as a minor product when the preparation of 3-Benzenesulfonyl-2-methylsulfanyl-pyrido[1,2-a]pyrimidin-4-ylideneamine was carried out in ethanol (example 2, method C). $^1$H NMR (500 MHz, CDCl$_3$): δ 9.67 (1H, br), 8.16 (1H, br), 8.03 (2H, d, 7.6 Hz), 7.69 (3H, m), 7.58(2H, t, 8.2 Hz), 4.55 (2H, q, 7.3 Hz), 1.30 (3H, t, 7.3 Hz).

Example 32

3-Benzenesulfonyl-2-methanesulfinyl-pyrido[1,2-a]
pyrimidin-4-ylideneamine

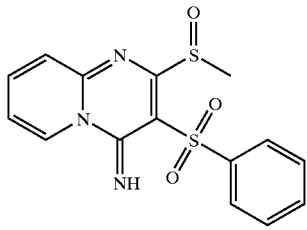

3-Benzenesulfonyl-2-methylsulfanyl-pyrido[1,2-a]pyrimidin-4-ylideneamine (50 mg, 0.15 mmol) was dissolved in anhydrous methylenechloride (2 ml) to which 3-chloroperoxybenzoic acid powder (32 mg, 50–60%, ~0.11 mmol) was added at 0° C. and stirred for 2 hours. In order to neutralize the reaction mixture, 2,6-tert-butyl-4-methylpyridine (38 mg, 90%, 0.17 mmol) was added. After concentration, the crude mixture was purified by preparative HPLC (XTerra™ MS C18 5.0 mM, MeOH/H$_2$O as the eluent) to yield 26 mg of product as a pale yellow solid.

$^1$H NMR (300 MHz, CDCl$_3$): δ 9.52 (1H, d), 9.34 (1H, br s), 8.04–7.94 (3H, m), 7.86–7.83 (1H, m), 7.64–7.61 (1H, m), 7.56–7.51 (2H, m), 7.29–7.28 (1H, m), 3.06 (3H, s).

Example 33

3-Benzenesulfonyl-2-methylsulfanyl-pyrido[1,2-a]
pyrimidin-4-ylidene)-methyl-amine

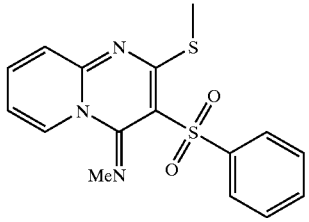

3-Benzenesulfonyl-2-methylsulfanyl-pyrido[1,2-a]pyrimidin-4-ylideneamine (100 mg, 0.30 mmol) was dissolved in anhydrous methylenechloride (1 ml). Methyl trifluoromethanesulfonate (74 mg, 0.45 mmol) was added at room temperature. The reaction was quenched with saturated aqueous NaHCO$_3$ at about 65% conversion. The crude product was extracted with methylenechloride and purified by preparative HPLC (XTerra™ MS C18 5.0 mM, MeOH/H$_2$O as the eluent) to yield 41 mg of product as an orange solid.

$^1$H NMR (300 MHz, CDCl$_3$): δ 8.91 (1H, d, J=7.0 Hz), 7.90–7.88 (2H, m), 7.77–7.71 (1H, m), 7.49–7.39 (3H, m), 7.05–7.00 (1H, m), 3.43 (3H, s), 2.33 (3H, s).

Example 34

N-(3-Benzenesulfonyl-2-methylsulfanyl-pyrido[1,2-a]pyrimidin-4-ylidene)-acetamide

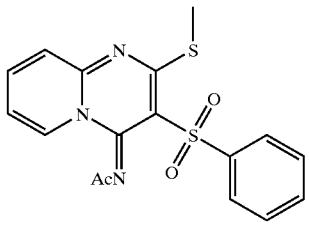

3-Benzenesulfonyl-2-methylsulfanyl-pyrido[1,2-a]pyrimidin-4-ylideneamine (100 mg, 0.30 mmol) was dissolved in anhydrous methylenechloride (2 ml) to which pyridine (48 mg, 0.6 mmol) was added. Acetylchloride was then added at room temperature and the reaction mixture was stirred overnight. The reaction was quenched with saturated aqueous NaHCO$_3$, extracted with methylene chloride, and purified by flash chromatography to yield 79 mg of a yellow solid product.

$^1$H NMR (300 MHz, CDCl$_3$): δ 8.99 (1H, d), 8.15–8.12 (1H, m), 7.94–7.88 (1H, m), 7.60–7.46 (3H, m), 7.26–7.17 (3H, m), 2.53 (3H, s), 2.30 (3H, s).

Example 35

3-Benzenesulfonyl-2-methylsulfanyl-pyrido[1,2-a]pyrimidin-4-one

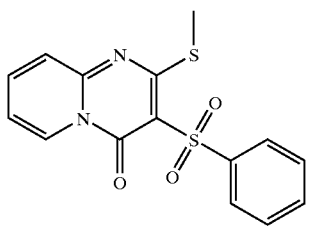

Methyl phenylsulfonylacetate (5 g, 23.3 mmol) was mixed with carbon disulfide (1.77 g, 23.3 mmol) in anhydrous DMSO (100 ml) at room temperature. Sodium hydride (60% in mineral, 1.2 g, 48.9 mmol) was added portionwise. After stirring at room temperature for 1 hour iodomethane (6.9 g, 48.9 mmol) was added neat and stirred overnight. The reaction mixture was quenched with water and extracted with methylene chloride. The crude product was purified via flash chromatography. 670 mg of the product (~2.1 mmol) was mixed with 2-aminopyridine (296 mg, 3.15 mmol) and $K_2CO_3$ (290 mg, 2.1 mmol) in DMF (2 ml). The reaction mixture was heated at 100° C. overnight then cooled to room temperature. The reaction mixture was diluted with methylene chloride (10 ml), washed with saturated aqueous NaCl, dried with $Na_2SO_4$ and concentrated. The product was an off white solid product, 30 mg, purified by preparative HPLC and flash chromatography.

$^1$H NMR (300 MHz, CDCl$_3$): δ 8.89 (1H, d, J=7.0 Hz), 8.21–8.18 (2H, d), 7.89–7.86 (1H, m), 7.57–7.47 (4H, m), 7.18–7.16 (1H, m), 2.58 (3H, s).

What is claimed is:

1. A compound of Formula I or a nontoxic pharmaceutically acceptable salt or solvate thereof,

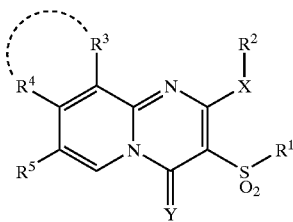

I wherein:
- $R^1$ is napthyl or phenyl, said phenyl optionally substituted with one to three substituents each independently selected from the group consisting of halogen, $C_{1-4}$ alkyl, and trifluoromethoxy;
- $R^2$ is 5-methylpyridin-2-yl or $C_{1-4}$ alkyl, said $C_{1-4}$ alkyl optionally substituted with hydroxy;
- $R^3$ is hydrogen, halogen, $C_{1-4}$ alkyl, or benzyloxy;
- $R^4$ is hydrogen or $C_{1-4}$ alkyl;
- the dashed line, taken with $R^3$ and $R^4$ together, optionally forms a 5 to 6 member aromatic ring structure having zero to 2 heteroatoms;
- $R^5$ is hydrogen, halogen, $C_{1-4}$ alkyl, benzyl, or $C(O)R^8$;
- X is $NR^6$, O, or $S(O)_m$;
- Y is $NR^7$ or O;
- m is 0, 1 or 2;
- $R^6$ is hydrogen or $C_{1-4}$ alkyl;
- $R^7$ is hydrogen, $C_{1-4}$ alkyl, or $C(O)C_{1-4}$alkyl; and
- $R^8$ is $C_{1-4}$ alkoxy, amino, ($C_{1-4}$ alkyl)amino, di($C_{1-4}$ alkyl)amino, or hydroxy.

2. The compound of claim 1 wherein X is S; and Y is $NR^7$.
3. The compound of claim 1 wherein X and Y are NH.
4. The compound of claim 1 wherein X is O; and Y is NH.
5. The compound of claim 1 wherein X is SO; and Y is NH.
6. The compound of claim 1 wherein X is S; and Y is O.
7. The compound of claim 1 selected from the group consisting of:

N-(3-benzenesulfonyl-4-imino-4H-pyrido[1,2-a]pyrimidin-2-yl)methylamine;
3-benzenesulfonyl-7-methyl-2-methylsulfanyl-pyrido[1,2-a]pyrimidin-4-ylideneamine;
N-(3-benzenesulfonyl-4-imino-4H-pyrido[1,2-a]pyrimidin-2-yl)ethylamine;
3-benzenesulfonyl-2-ethoxy-pyrido[1,2-a]pyrimidin-4-ylideneamine;
3-benzenesulfonyl-7-bromo-9-methyl-2-methylsulfanyl-pyrido[1,2-a]pyrimidin-4-ylideneamine;
3-benzenesulfonyl-9-bromo-7-methyl-2-methylsulfanyl-pyrido[1,2-a]pyrimidin-4-ylideneamine;
3-(3,4-dichloro-benzenesulfonyl)-2-methylsulfanyl-pyrido[1,2-a]pyrimidin-4-ylideneamine;
N-(3-benzenesulfonyl-2-methylsulfanyl-pyrido[1,2-a]pyrimidin-4-ylidene)methylamine;
3-(2-chloro-benzenesulfonyl)-2-methylsulfanyl-pyrido[1,2-a]pyrimidin-4-ylideneamine;
3-benzenesulfonyl-2-methylsulfanyl-pyrido[1,2-a]pyrimidin-4-ylideneamine;
3-(4-fluoro-benzenesulfonyl)-2-methylsulfanyl-pyrido[1,2-a]pyrimidin-4-ylideneamine;
2-(3-benzenesulfonyl-4-imino-4H-pyrido[1,2-a]pyrimidin-2-ylamino)ethanol;
3-benzenesulfonyl-2-methanesulfinyl-pyrido[1,2-a]pyrimidin-4-ylideneamine;
3-benzenesulfonyl-7-chloro-2-methylsulfanyl-pyrido[1,2-a]pyrimidin-4-ylideneamine;
3-(4-chloro-benzenesulfonyl)-2-methylsulfanyl-pyrido[1,2-a]pyrimidin-4-ylideneamine;
3-benzenesulfonyl-7-fluoro-2-methylsulfanyl-pyrido[1,2-a]pyrimidin-4-ylideneamine;
3-benzenesulfonyl-9-methyl-2-methylsulfanyl-pyrido[1,2-a]pyrimidin-4-ylideneamine;
3-benzenesulfonyl-9-benzyloxy-2-methylsulfanyl-pyrido[1,2-a]pyrimidin-4-ylideneamine;
3-benzenesulfonyl-8-methyl-2-methylsulfanyl-pyrido[1,2-a]pyrimidin-4-ylideneamine;
3-benzenesulfonyl-7-bromo-2-methylsulfanyl-pyrido[1,2-a]pyrimidin-4-ylideneamine;
2-methylsulfanyl-3-(4-trifluoromethoxy-benzenesulfonyl)-pyrido[1,2-a]pyrimidin-4-ylideneamine;
3-benzenesulfonyl-4-imino-2-methylsulfanyl-4H-pyrido[1,2-a]pyrimidine-7-carboxylic acid methyl ester;
3-benzenesulfonyl-2-methylsulfanyl-pyrimido[2,1-a]isoquinolin-4-ylideneamine;
3-(4-chloro-2,5-dimethyl-benzenesulfonyl)-2-methylsulfanyl-pyrido[1,2-a]pyrimidin-4-ylideneamine;
3-benzenesulfonyl-2-methylsulfanyl-pyrido[1,2-a]pyrimidin-4-one;
7-benzenesulfonyl-6-methylsulfanyl-4,5,8a-triaza-phenanthren-8-ylideneamine;
2-methylsulfanyl-3-(naphthalene-2-sulfonyl)-pyrido[1,2-a]pyrimidin-4-ylideneamine;
3-benzenesulfonyl-7-benzyl-9-methyl-2-methylsulfanyl-pyrido[1,2-a]pyrimidin-4-ylideneamine;

(3-benzenesulfonyl-4-imino-7-methyl-4H-pyrido[1,2-a]
pyrimidin-2-yl)-(5-methyl-pyridin-2-yl)amine;
3-(4-tert-butyl-benzenesulfonyl)-2-methylsulfanyl-pyrido
[1,2-a]pyrimidin-4-ylideneamine;
3-benzenesulfonyl-2-methylsulfanyl-8-propyl-pyrido[1,2-a]
pyrimidin-4-ylideneamine;
N-(3-benzenesulfonyl-2-methylsulfanyl-pyrido[1,2-a]
pyrimidin-4-ylidene)acetamide;
3-benzenesulfonyl-4-imino-2-methylsulfanyl-4H-pyrido[1,
2-a]pyrimidine-7-carboxylic acid amide; and
3-benzenesulfonyl-8-ethyl-2-methylsulfanyl-pyrido[1,2-a]
pyrimidin-4-ylideneamine; or a nontoxic pharmaceutically acceptable salt thereof.

8. A pharmaceutical composition comprising a therapeutically effective amount of a compound as defined in claim 1 and a pharmaceutically acceptable carrier, adjuvant or diluent.

9. A method of treating a disorder responsive to antagonism of the 5-$HT_6$ receptor, in a mammal in need of such treatment, comprising administering to the mammal a therapeutically effective amount of a compound of claim 1 wherein said disorder is psychoses, depression, cognition enhancement, Parkinson's disease, and Alzheimer's disease.

* * * * *